United States Patent
Yokoi et al.

(10) Patent No.: US 6,855,111 B2
(45) Date of Patent: Feb. 15, 2005

(54) CAPSULE ENDOSCOPE

(75) Inventors: Takeshi Yokoi, Hino (JP); Akira Hasegawa, Musashino (JP); Shinya Matsumoto, Machida (JP); Takayuki Suzuki, Hachioji (JP); Hidetake Segawa, Hachioji (JP); Hironobu Takizawa, Hachioji (JP)

(73) Assignee: Olympus Corporation, Tokyo (JP)

(*) Notice: Subject to any disclaimer, the term of this patent is extended or adjusted under 35 U.S.C. 154(b) by 179 days.

(21) Appl. No.: 10/382,501

(22) Filed: Mar. 7, 2003

(65) Prior Publication Data

US 2003/0171653 A1 Sep. 11, 2003

(30) Foreign Application Priority Data

Mar. 8, 2002 (JP) ........................................ 2002-064019

(51) Int. Cl.[7] .................................................. A61B 1/06
(52) U.S. Cl. ........................ 600/179; 600/160; 600/177; 348/68
(58) Field of Search .......................... 600/109, 176–180, 600/160; 362/800; 348/68

(56) References Cited

U.S. PATENT DOCUMENTS

| | | | |
|---|---|---|---|
| 4,272,156 A | * | 6/1981 | Ishibashi et al. ............ 385/117 |
| 6,251,068 B1 | * | 6/2001 | Akiba et al. ................ 600/182 |
| 2002/0068853 A1 | * | 6/2002 | Adler ......................... 600/160 |
| 2003/0120130 A1 | * | 6/2003 | Glukhovsky et al. ....... 600/109 |
| 2003/0130562 A1 | * | 7/2003 | Barbato et al. ............. 600/109 |
| 2004/0171914 A1 | * | 9/2004 | Avni .......................... 600/160 |

FOREIGN PATENT DOCUMENTS

| | | |
|---|---|---|
| JP | 2001-91860 | 4/2001 |
| WO | WO 00/76391 A1 | 12/2000 |

* cited by examiner

Primary Examiner—John P. Leubecker
(74) Attorney, Agent, or Firm—Arnold International; Bruce Y. Arnold (57) ABSTRACT

A capsule endoscope is provided with lighting means for illuminating the interior of a living body, an image pickup means for capturing an image of a site illuminated by the lighting means, and a transparent cover which houses the image pickup means and the lighting means within a sealed, cylindrical-shaped capsule case. The image pickup means includes an objective optical system having a depth of field. An object within the depth of field of the objective optical system is illuminated more evenly than possible with a single lighting means by arranging multiple lighting means at the periphery of the objective optical system and causing the beams from individual lighting means to overlap in specified ways so that a nearly uniform illumination of an object of interest is achieved. Light diffusers may be employed to diffuse the light from the light sources, and a color correction filter may be used.

15 Claims, 8 Drawing Sheets

CAPSULE ENDOSCOPE

BACKGROUND OF THE INVENTION

Recently, endoscopes have found wide use in medical fields and in industry. More recently, the pain that is normally associated with the use of an endoscope has been eliminated for some endoscope applications by the development of a capsule endoscope. Japanese Laid-Open Patent Application 2001-91860 is one example of such an endoscope, wherein an objective optical system, image pickup, and light source are contained within a capsule that is swallowed by a patient. The light source employs light emitting elements that are symmetrically arranged within a nearly semi-spherical transparent cover, and objects that are positioned within an observation range illuminated by the light emitting elements are imaged by the objective optical system onto the image pickup.

In the above-mentioned patent publication, an objective lens system and two illuminators are fixed inside the nearly semi-spherical transparent cover, and a lens barrel which supports the objective lens system is moved for focus adjustment and then is fixed in position with a fixing screw. When multiple light emitting elements are arranged at the periphery of an objective optical system, as in the above-mentioned patent publication, observation and diagnosis are made difficult if there exists any offset or change in the illumination onto an irradiated surface. Moreover, in a coelomic observation, sometimes inner wall parts of lumens, such as the esophagus and the intestinal canal, etc., are the objects of interest for observation, in which case the periphery of the field of view of the objective optical system must be brightly illuminated rather than near the center of the field of view. On the other hand, sometimes a gastric wall, or some other object in a relatively large space such as the stomach, is taken as the object of observation wherein it is desirable to brightly illuminate an area near the center of the field of view.

Furthermore, dust or particles such as shaving dregs created when a lens frame is moved when performing an initial focus adjustment of the objective optical system can easily settle on the image surface of the image pickup, causing the likelihood to be too high that images detected by the image pickup will be degraded.

BRIEF SUMMARY OF THE INVENTION

The present invention relates to a capsule endoscope which is to be swallowed in order to inspect portions of the interior of a living body, and enables an object that is located within the depth of field of an objective optical system of the capsule endoscope to be illuminated with a nearly uniform illumination distribution. Furthermore, the present invention provides a capsule endoscope that prevents dust, such as shaving dregs of a lens frame that may be produced in performing a focus adjustment, from attaching to the front side of the image pickup and degrading the detected image.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

A capsule endoscope according to the present invention is provided with lighting means for illuminating the interior of a living body, an image pickup means for capturing an image of a site illuminated by the lighting means, and a transparent cover which houses the image pickup means and the lighting means within a sealed, cylindrical-shaped capsule case. The image pickup means includes an objective optical system having a depth of field. An object within the depth of field of the objective optical system is illuminated more evenly than possible with a single lighting means by arranging multiple lighting means at the periphery of the objective optical system and causing the beams from individual lighting means to overlap in specified ways so that a nearly uniform illumination of an object of interest is achieved.

Moreover, a construction is provided whereby the front of an image pickup means is covered prior to making an initial focus adjustment. As mentioned previously, this prevents dust and shaving dregs of a lens frame, etc. produced in performing a focus adjustment, from attaching to the front surface of the image pickup and degrading the image that is detected.

Several embodiments of the present invention will now be described in detail.

Embodiment 1

Figures 1A, 1B:
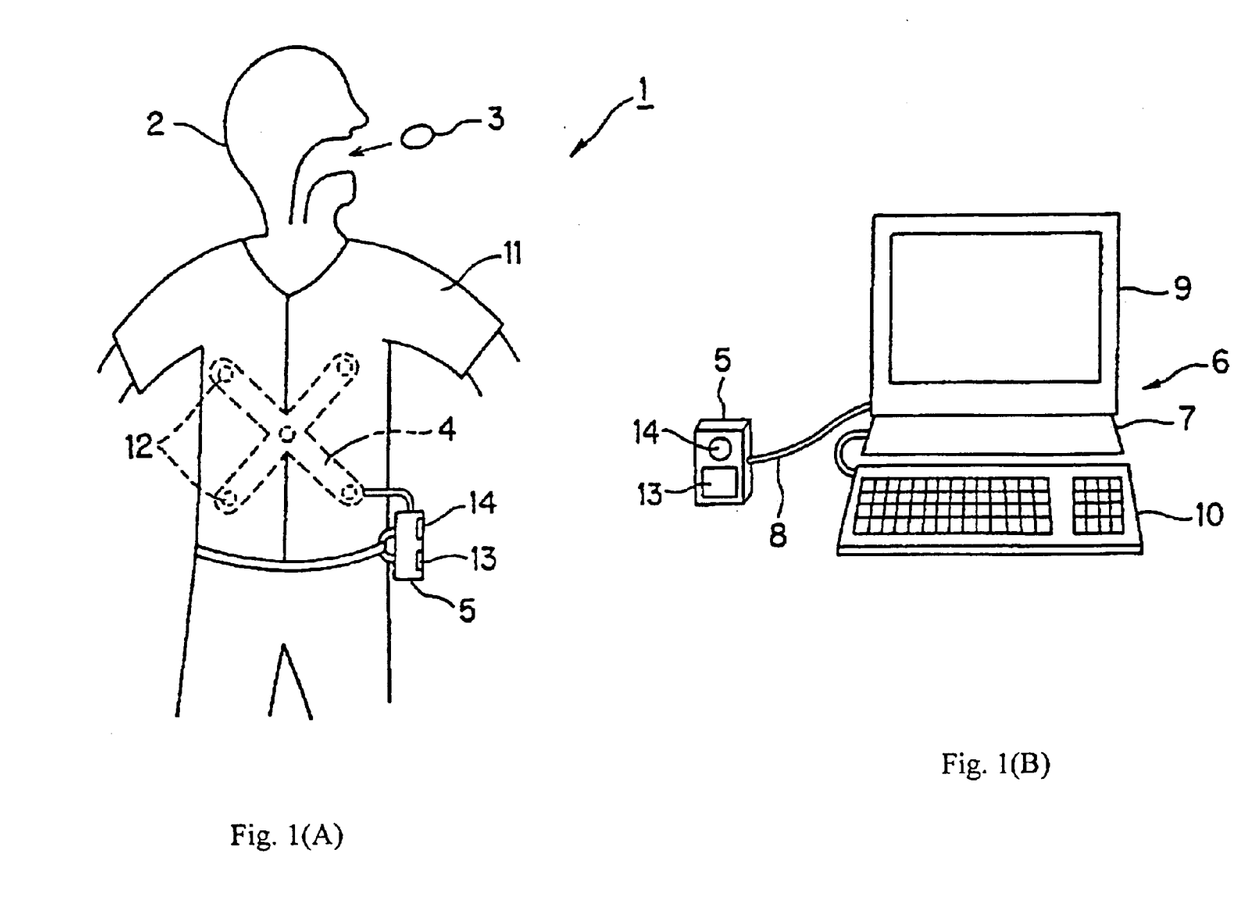
FIGS. 1(A) and 1(B) show a capsule endoscope system that employs a capsule endoscope according to Embodiment 1 of the present invention.

This embodiment will be discussed with reference to FIGS. 1(A)–6(B). As shown in FIG. 1(A), a capsule endoscope system 1 employs a capsule endoscope 3 which transmits an image signal that is obtained by optically imaging an inner surface of a coelomic canal, detecting the image with an image detecting element, wirelessly transmitting the detected image signal to an external unit 5 which receives, via an antenna unit 4, electromagnetic signals transmitted by the capsule endoscope 3. The antenna unit 4 is provided outside the body of a patient 2, and the external unit functions to temporarily store the image information that is received using, for example, a hard disc of compact flash (R) size having a memory capacity of, for example, 1 GB.

As shown in FIG. 1(B), the external unit 5 may be detachably connected via a communication cable, such as USB cable 8, to a personal computer (hereinafter PC) 7. Image data accumulated in the external unit 5 can be transferred to a display system 6 in order to display the images from the capsule endoscope or they may be archived onto the PC's hard drive for later viewing. Images that are temporarily stored in the external unit 5 can thus be transferred to the hard disc of the PC and displayed on the display unit 9. A keyboard 10 may be connected to the PC 7 in order to input data and to control the operation of the PC 7.

The communications cable can be in accordance with any of the communication specifications USB1.0, USB1.1, USB2. In addition, other serial communication cables such as those performing serial data communication according to the RS-232C or IEEE 1894 specifications may also be used. Moreover, the communications cable is not limited to serial data communication, as cables which employ parallel data communication may also be used.

As shown in FIG. 1(A), when the capsule endoscope 3 is swallowed to begin an endoscopic examination, an antenna unit 4 that includes multiple antennas 12 is mounted to the inner side of a shielding shirt 11 that includes multiple conductors. The purpose of the shielding shirt which the patient wears is to reduce electromagnetic interference (i.e., noise) that otherwise would be picked-up by the antennas. Images that are captured by the capsule endoscope 3 are transmitted using an antenna that is built into the capsule, and these signals are received by the antennae unit 4 and transferred to the external unit 5. The external unit 5 may be detachably attached to the antennae 4 and is supported, for example, by a belt worn by the patient.

The external unit 5 is, for example, box-shaped and may be provided with a liquid crystal monitor 13 on its front surface for displaying images received from the capsule endoscope. Components of the external unit 5 include an operating button 14 for performing a control operation, as well as other components (not illustrated) such as a communication circuit, a control circuit, an image data display circuit, and a power source.

Figure 2:
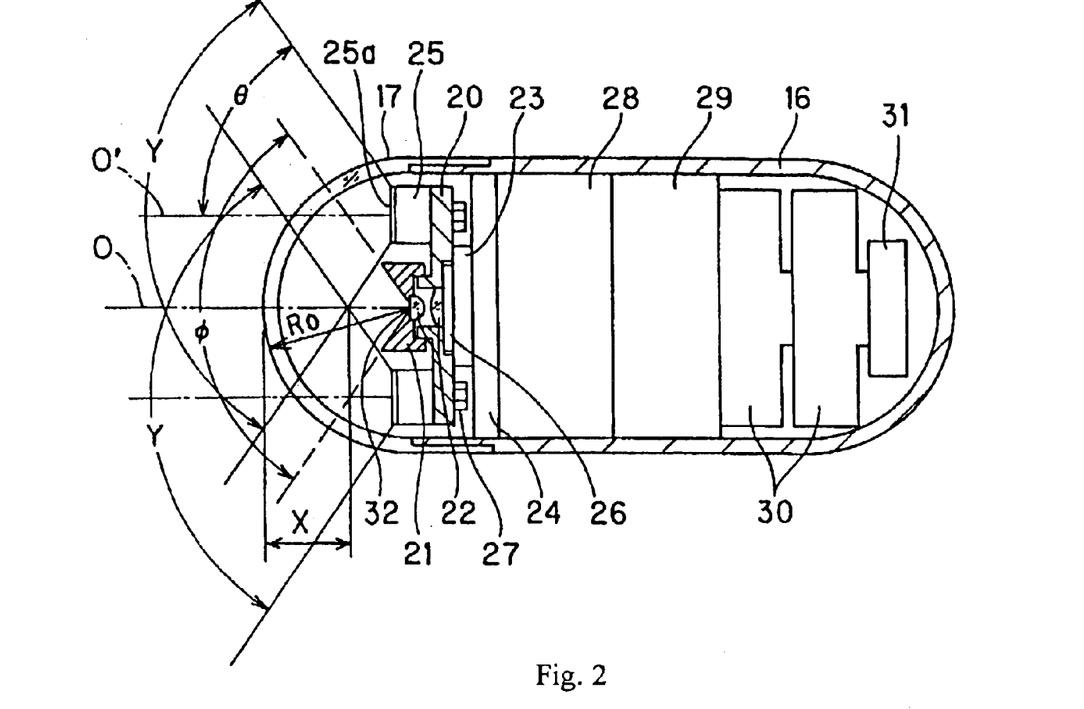
FIG. 2 is a cross-sectional diagram showing the components of a capsule endoscope according to Embodiment 1 of the present invention.

FIG. 2 shows a capsule endoscope according to Embodiment 1 of the present invention. A semi-spherical transparent cover 17 is sealed in a water-tight manner to a cylindrical capsule endoscope body 16. The rear end of the capsule endoscope is rounded, and the following components are contained within the capsule endoscope body: a lens frame 21, an objective optical system 22 and a CMOS image pickup device 23. The objective optical system is formed by fitting a first lens and a second lens within a tube that is supported by a substrate 20. The substrate 20 and tube may be integrally formed as one unit, and the tube is arranged about a central axis of the cylindrical capsule endoscope body behind the transparent cover 17. The CMOS image pickup device 23 is arranged at the image surface of the objective optical system 22. The CMOS image pickup device 23 is fitted to the front surface of the substrate 24. Moreover, white LEDs 25 are fitted as lighting means around the objective optical system 22 at two or more locations in front of the substrate 20, symmetrically about the objective optical system 22.

Furthermore, a color correction filter 26 for protecting the image sensor surface of the CMOS image pickup device 23 and for correcting lighting characteristics of the white LEDs 25 is fitted in front of the image pickup surface. Also, the second lens, in order from the object side, of the objective optical system 22 is positioned immediately in front of the color correction filter 26. Furthermore, electronic chips 27 containing LED driving circuits for intermittently powering the LEDs 25 so that they emit flashes at controllable intervals are mounted around the CMOS image pickup device 23 on the substrate 20.

A drive processing circuit 28 for driving the CMOS image pickup device 23 and for performing signal processing of the signals output from the CMOS image pickup 23 is arranged to the rear of substrate 24. A wireless communication circuit 29 for modulating image signals produced by the drive processing circuit 28 at a high frequency so that they may be transmitted by electromagnetic waves is positioned behind the drive processing circuit 28, and two button-shaped batteries 30 are provided behind the wireless communication circuit 29. The batteries serve as a built-in power source for operating the LED driving circuit, the drive processing circuit 28 and the wireless communication circuit 29, and are arranged by stacking the batteries 30 in the axial direction of the capsule container. An antenna 31, that is fed by the wireless communication circuit 29, is arranged adjacent to the batteries 30 inside the rear end of the capsule container.

In this embodiment, the transparent cover 17 is hemispherical in shape. Both the inner and outer surfaces of the transparent cover have a common center of curvature, and the entrance pupil of the objective optical system 22 is positioned at this common center of curvature. The multiple white LEDs 25, by being positioned remote from the common center of curvature (i.e., at the periphery of the objective optical system) do not cause ghost images and flare in the images detected by the axially centered CMOS image pickup even when a portion of the illuminating light is reflected by the inner surface of the transparent cover.

Moreover, in this embodiment, the light detecting surface of the CMOS image pickup device 23 is protected by a color correction filter 26, and the substrate 20 is fitted with the second lens, in order from the object side, of the objective optical system 22, so that the second lens is mounted so as to be immediate adjacent to and cover the color correction filter 26. A lens frame 21 that is fitted to a tube of the substrate 20 is initially adjusted in position along the optical axis O to so that a proper focus is obtained.

Therefore, this embodiment prevents the adherence of dust, such as shavings of the lens frame 21 produced by movement during focus adjustment, etc., to the front of the image pickup surface of the CMOS image pickup 23 even if such dust is generated at the time of focusing.

Moreover, in this embodiment, blue light emissions can be converted to longer wavelengths so as to obtain higher output white LEDs 25 by using a fluorescent coating on the light-emitting surface of the white LEDs 25. Also, a diffusing plate 25a that includes fluorescent resin may be bound to the LEDs 25 for providing a diffusion action so that light rays emitted by the white LEDs 25 can be diffused by the diffusing plate 25a so as to emit more divergent light beams (i.e., light beams having wider angles of emitted light).

Furthermore, in this embodiment, as shown in FIG. 2, the illuminating rays of the multiple white LEDs 25 that are arranged at the periphery of the objective optical system 22 are set up so that their light beams overlap before reaching the near-point of the depth of field of the objective optical system 22. In this way, an object that is positioned within the depth of field of the objective optical system can be illuminated more evenly than if a single white LED 25 were used as an illuminating means. This facilitates the observation of objects and improves contrast for diagnosing an affected part. In FIG. 2, the near point on the optical axis O of the depth of field of the objective optical system is set to the outer surface of the transparent cover (of radius Ro), and the point that the two beams intersect is at a distance X inside the outer surface of the transparent cover, as illustrated. Moreover, the position of the entrance pupil 32 in FIG. 2, is at the center of curvature of the outer and inner surfaces of the transparent cover 17.

In the case of FIG. 2, the illuminating rays of the white LEDs 25 at the upper and lower side of the objective optical system begin overlapping at a distance X from the outer surface of the transparent cover 17, as measured along the optical axis toward the objective optical system. The central axis of light emission from the upper one of the LEDs 25 is shown by O'.

Figure 3:
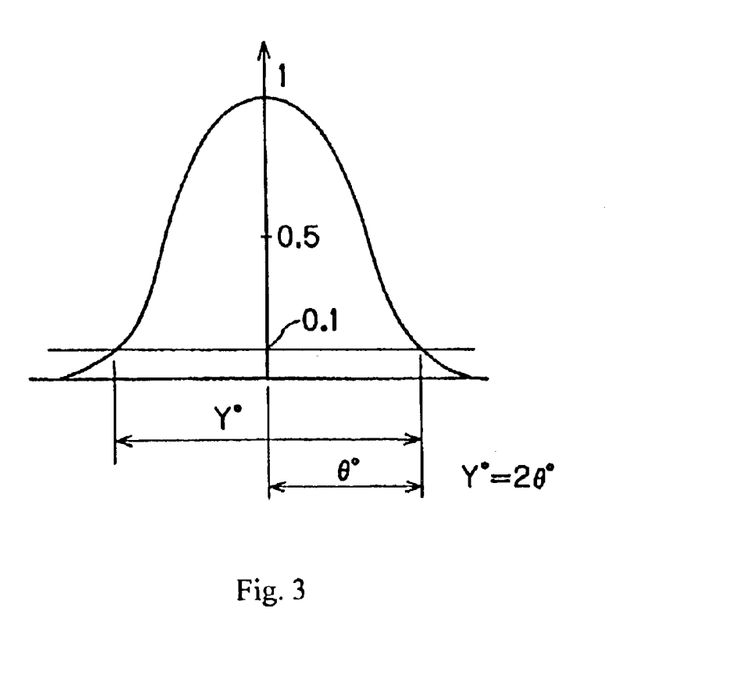
FIG. 3 shows the normalized intensity distribution of illuminating rays (Y-axis) versus the angle (X-axis) such rays make with the central axis of a light source when diffusing plates are used to diffuse the light from the light source, with θ being the half-beam angle, in degrees, as measured at 0.1 of the peak intensity, and Y being the angle of light distribution, where Y=2θ.
Figure 4:
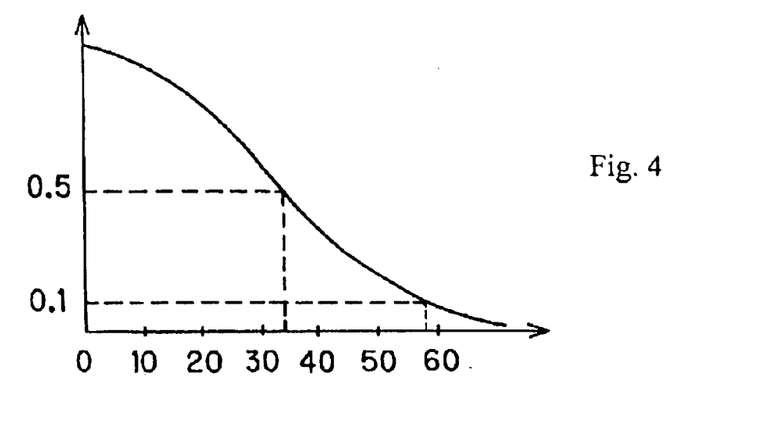
FIG. 4 shows, in more detail, the normalized intensity distribution shown in FIG. 3, but illustrates the half-beam angles when measured at 0.5 of the peak intensity and at 0.1 of the peak intensity.
Figure 5:
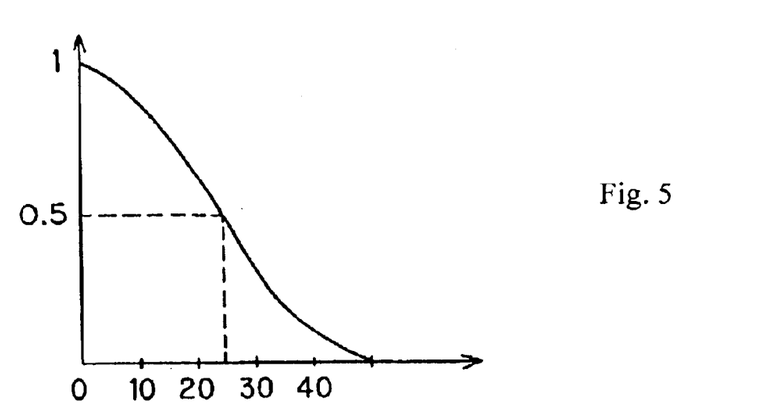
FIG. 5 shows the normalized intensity distribution of illuminating rays (Y-axis) versus the angle (X-axis) such rays make with the optical axis when a diffusing plate is not used.

FIGS. 3–5 show the normalized light intensity (Y-axis) as a function of the angle of emergence (X-axis) for various situations.

As shown in FIG. 3, when the intensity is taken as unity at an angle of emergence of 0 degrees, the intensity profile follows a Gaussian distribution, decreasing with increasing angle of emergence. If the half-beam angle θ is measured from on-axis (emergence angle equals zero) to the point that the normalized intensity has fallen to 0.1, then double of this angle is the full-beam angle Y, shown in FIG. 3. This embodiment is characterized by the fact that, when a surface to be illuminated is perpendicular to the optical axis O of the objective optical system 22, and multiple white LEDs 25 are arranged at the periphery of the objective optical system 22 so that the illumination distribution within the visual field at the surface to be illuminated becomes nearly constant, light rays of the white LEDs 25 having a relative intensity 0.1 overlap nearer the objective optical system than is the near point of the depth of field of the objective optical system.

If uneven illumination exists at the illuminated surface, observation and an accurate diagnosis will be more difficult than if the illumination is even. Therefore, multiple light-emitting elements are arranged at the periphery of the objective optical system 22, as in this embodiment, so as to provide for a more even illumination. Moreover, in coelomic observations, sometimes inner wall parts of lumens such as the esophagus or intestinal canal, etc., are taken as objects of observation and the periphery of the visual field rather than an object near the center of the visual field must be clearly illuminated. On the other hand, sometimes a gastric wall in a relatively wide space, such as the stomach, is the object of observation, and a region at or near the center of the visual field must be clearly illuminated. Accordingly, in the capsule endoscope of this invention, when the surface of an illuminating optical system is set up perpendicular to the optical axis of the objective optical system, the above multiple light-emitting elements are arranged at the periphery of the objective optical system so that the illumination distribution is nearly constant. In this way, either of the above observation states can be satisfactorily observed.

In the rays emerging from the white LEDs, rays with a larger angle of emergence than a given emergence angle have very little influence on the illumination distribution at an illuminated surface, and rays with a smaller angle of emergence than a given emergence angle have a great influence on the illumination distribution at an illuminated surface. More particularly, there is a range of emergent angles about the central axis of each LED which makes a particularly strong contribution to the illumination distribution at an illuminated surface. Generally, if the light distribution follows a Gaussian distribution, about 75% of the total light emitted is emitted with a relative intensity ratio of 0.5 or higher. This light exerts a strong influence on the illumination distribution of an illuminated surface.

LEDs wherein an optical window having a convergence effect is placed over the light-emitting surface have been known. Rays emergent from such an LED generally have a light-distribution characteristic with a strong directivity, as seen in FIG. 5. As shown in FIG. 5, the half-beam angle, as measured for rays having a normalized intensity ratio of 0.5 or higher, is about 25° (giving a full beam width of about 50°, as measured between the 0.5 relative intensity points). Thus, as discussed previously, light rays having an emergent angle within 25° of the central axis of a light source exert a large influence on the illumination distribution at the surface of an illuminated object. Accordingly, if light rays from multiple white LEDs having an angle of emergence within about 25° of the central axis of a light source intersect at a distance from the LEDs that is nearer than the near point of the depth of field of the objective optical system, the illumination distribution at the illuminated surface within the depth of field will be substantially constant.

In a capsule endoscope, it is preferable to widen the angle of the visual field of the objective optical system so that a viewing range as wide as possible can be observed. For the objective optical system of the capsule endoscope of the present invention, full field of view has an angular beam width Φ in the range of 90°–140°; however, it is difficult to keep the illumination distribution substantially constant over such a wide angle.

For light emitting elements to be used with an objective optical system 22 having a wide-angle field of view as described above, it is preferable to provide a diffusing plate 25a in front of each light emitting surface of the LEDs in order to provide a more diffused, light distribution characteristic as shown in FIG. 4.

Figure 6A:
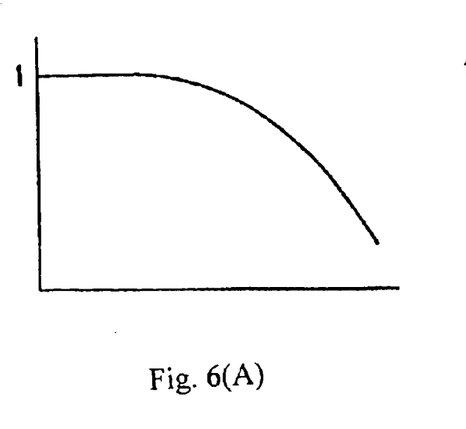
FIGS. 6(A) and 6(B) are graphs showing examples of the normalized illumination at a plane (that is perpendicular to the cylinder axis of the capsule endoscope and located within the depth of field of the objective optical system) that is illuminated by multiple light sources, with FIG. 6(A) illustrating the situation when rays (from two LEDs 25 with diffusion plates 25a as illustrated in FIG. 2) having a normalized intensity ratio of 0.5 are made to intersect prior to reaching the near point of the depth of field of the objective optical system, and with FIG. 6(B) illustrating the situation when rays (from two LEDs 25 with diffusion plates 25a as illustrated in FIG. 2) having a normalized intensity ratio of 0.1 are made to intersect prior to reaching the near point of the depth of the objective optical system.

In this case, the half-beam width, as measured between the points where the relative intensity has fallen to 0.5, is about 34°, and the half-beam width, as measured between the points where the relative intensity has fallen to 0.1 is about 58°. It is known that light beams, from two white LEDs 25 with diffusers 25a that are arranged at the periphery of an objective optical system of a capsule endoscope, will intersect before the near point of the depth of field of an objective optical system 22 is reached in the case that the point of intersection of the beams is measured at the 0.5 normalized intensity points. In other words these rays intersect in a space on the objective optical system side of the near-point of the effective depth of field of the objective optical system 22. The illuminated surface distribution then becomes as shown in FIG. 6(A), with an even illumination intensity being provided in the vicinity of the center of the visual field, but with the illumination intensity suddenly darkening at the periphery of the visual field.

Figure 6B:
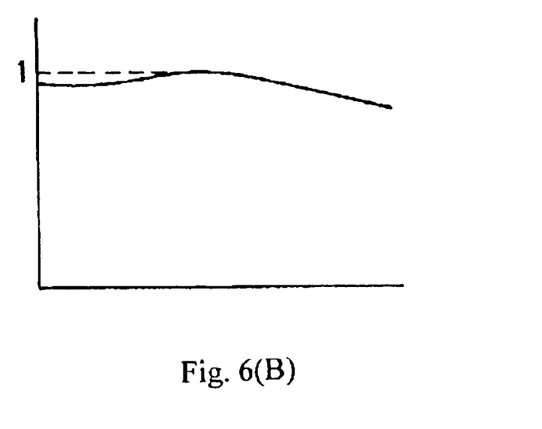

On the other hand, FIG. 6(B) illustrates an illumination distribution of the illuminated surface when the LEDs are oriented so that their beam centers are directed slightly outward. In FIG. 6(B), the LEDs 25 with diffusers are directed so that their light beams, as measured at the 0.1 intensity points, intersect before the near point of the effective depth of field of the objective optical system 22 is reached.

In the illumination distribution of FIG. 6(B), the illumination is only slightly reduced in the vicinity of the center of the illuminated surface and the illumination is only slightly reduced at the periphery of the visual field. Thus, generally speaking, the illumination is made rather uniform, without any sharp decrease in illumination throughout the illuminated surface. Therefore, an appropriate, almost uniform illumination over the whole visual field can be obtained. Accordingly, this embodiment provides bright observation images over the entire visual field and the images are easy to diagnose.

Moreover, it is desirable that the position where the optical axis of the objective optical system 22 and the outer surface of the transparent cover 17 intersect be included within the effective depth of field of the objective optical system 22, in that objects that are immediately adjacent the front surface throughout the field of view need to be able to be imaged by the objective optical system 22 for capture by the capsule endoscope.

For this reason, it is taken as a condition for performing an appropriate illumination that rays having an angle of emergence of about 58° from the multiple white LEDs 25, (i.e., rays with an intensity ratio 0.1, as shown in FIG. 4) intersect nearer the objective optical system than the outer surface of the transparent cover 17 as shown in FIG. 2.

Thus, this embodiment enables an almost uniform illumination of an object within the depth of field because illuminating rays given by the multiple illuminating means arranged at the periphery of the objective optical system 22 are oriented with their beam axes directed slightly outward but with the point of intersection of the beams being nearer the objective optical system than is the near point of the depth of field of the objective optical system 22. This facilitates the observation of an object and provides an image having sufficient contrast for diagnosing an affected part. Moreover, means for correcting the emission angle (such as lenses, etc.) of the illumination means when using light-emitting elements such as white LEDs 25 in order to match with the visual field of the objective optical system may be added, and lighting means other than the white LEDs 25 may also be used.

Furthermore, the lighting system of a capsule endoscope 3 containing light-emitting elements may also be provided with a mechanism for adjusting the light-emitting intensity of the light-emitting elements so that the illumination of an object can be made appropriate for the circumstances. In addition, a color correction filter 26 may be arranged in front of the image sensor surface of the image pickup, for example, a CMOS image pickup 23, but the filter may be provided elsewhere, such as in the objective optical system 22, on the inner surface of said transparent cover 17, in front of the white LEDs 25, and so on.

In this embodiment, the position of the front surface of the white LEDs 25 is forward of a plane that passes through the most object side of the objective optical system 22, but this relationship may be switched. The objective optical system 22 is constructed of two plano-convex lenses, in order from the object side, with the planar surface of the first lens being on the object side and with the planar surface of the second lens being on the image side. However, these lenses may instead be meniscus-shaped with positive optical power, with the front surface of the first lens being concave and having a larger radius of curvature than the rear surface of the first lens.

When a meniscus lens of positive optical power and a plano-convex lens with positive optical power are combined to form the objective optical system 22, the astigmatism (as compared with the case of the objective optical system 22 being constructed of two plano-convex lenses) at the periphery of the visual field can be reduced so as to provide a higher quality image.

Embodiment 2

Figure 7:
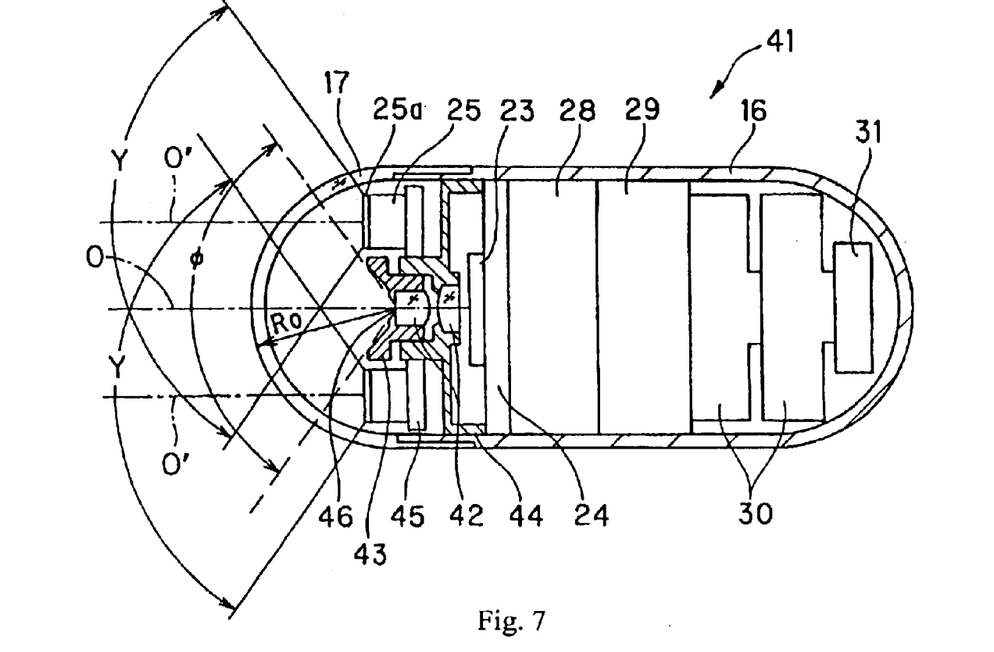
FIG. 7 is a cross-sectional diagram showing the components of a capsule endoscope according to Embodiment 2 of the present invention.

FIG. 7 illustrates Embodiment 2 of the present invention. In the capsule endoscope 41 of Embodiment 2, just as in Embodiment 1, a semi-spherical transparent cover 17 is connected to the front end of a cylindrical outer case 16 so as to be water-tight. The rear end of the cylindrical outer case 16 has a rounded shape and the following components are accommodated within the closed capsule. A lens frame 43 is fitted with a first lens, in order from the object side, of an objective optical system 42. The lens frame 43 is mounted about the center axis O of the cylindrical outer case 16 by fitting it within a central bore of a sealing cover 44 which serves as a lens frame for mounting the second lens, in order from the object side, of the objective optical system 42. At the image position of the objective optical system 42, a CMOS image pickup device 23 is mounted to the front side of a substrate 24. The surface of the image pickup device 23 is protected by the sealing cover 44 and the second lens which is held by the sealing cover 44 so that its rear surface is separated a short distance from the CMOS image pickup device 23.

Although the second lens is mounted in the central part of the sealing cover 44, and serves to protect the surface of the CMOS image pickup device 23, the CMOS image pickup device 23 could instead use a cover glass for this purpose in lieu of using the sealing cover.

White LEDs 25 are mounted to the front side of the substrate 45 at multiple locations, such as in symmetrical positions about center axis O and at the periphery of the objective optical system 42. A diffusing plate 25a is mounted to each of these white LEDs. A drive processing circuit 28 and other components are positioned on the rear side of the substrate 24, as described previously for Embodiment 1.

Furthermore, in this embodiment, the axial position of the entrance pupil 46 of the objective optical system 42 is positioned coincident with the centers of curvature of the inner surface and the outer surface of the transparent cover 17 so as to avoid undesired rays from the illumination means from entering the objective optical system 42. The radius of curvature of the outer surface of the transparent cover 17 is labeled in FIG. 7 as Ro. In this embodiment, the illuminating rays from the multiple white LEDs 25 that are arranged at the periphery of the objective optical system 42 overlap prior to reaching the near-point of the depth of field of the objective optical system 42. In this embodiment, the near point coincides with the outer surface of the transparent cover 17.

In this embodiment, the sealing cover 44, with the second lens of the objective optical system 42 affixed thereto, is mounted so as to protect the image pickup device 23 before any focus adjustment of the objective optical system 42 is made. Subsequently, the lens frame 43 with the first lens mounted therein is slid into the cental bore of the sealing cover and slid in the direction of the optical axis so as to perform a focus adjustment. After the focus adjustment, the lens frame 43 is fixed to the tube of the sealing cover 44 with an adhesive.

Accordingly, this embodiment can avoid dust or other particles generated by the focus adjustment from obscuring the image sensor surface of the CMOS image pickup device 23. In this manner, degradation in the quality of a detected image resulting from dust or shavings of the lens frame that occurs during an initial focus adjustment step is avoided. Other constructions and functions are the same as for Embodiment 1 and will not be further discussed.

Embodiment 3

Figure 8:
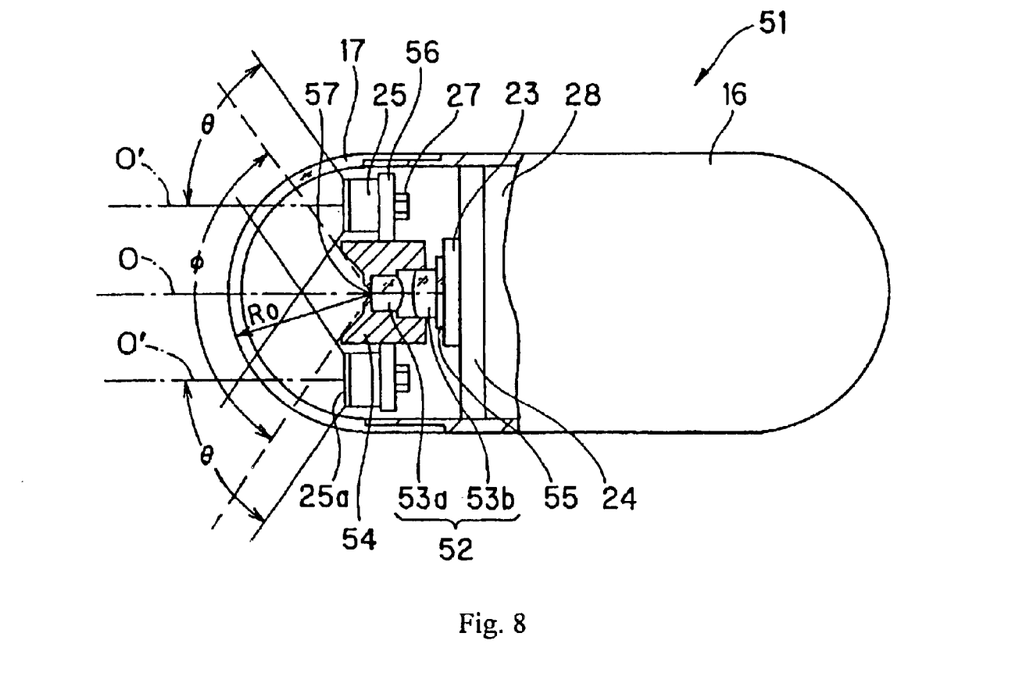
FIG. 8 is a cross-sectional diagram showing the components of a capsule endoscope according to Embodiment 3 of the present invention.

FIG. 8 illustrates Embodiment 3 of the present invention. Like the capsule endoscope 41 shown in FIG. 7, the capsule endoscope 51 of Embodiment 3 has a semi-spherical transparent cover 17 that is connected and sealed in a water-tight manner to the front end of an outer cylindrical case 16. A lens frame 54 that is fitted with a first lens 53a, in order from the object side, of an objective optical system 52 is focused and then fixed to the second lens 53b of the objective optical system 52. A second lens 53b, in order from the object side, of an objective optical system 52 is mounted to a cover glass 55 which covers a CMOS image pickup device 23 that is mounted to the front surface of a substrate 24.

More specifically, the second lens 53b is cemented using a transparent adhesive, or the like, and is fixed to the front surface of a cover glass 55 mounted so as to protect the image sensor surface of the CMOS image pickup device 23. The lens frame 54 has an inner diameter that is attached to the outer diameter of the second lens 53b. The second lens 53b is affixed to the cover glass 55. The lens frame 54 with the first lens 53a attached is slid in the direction of the cylinder axis O in order to perform focus adjustment of an image formed by the objective optical system 52 so that the image is precisely focused at the image sensor surface of the CMOS image pickup 23 device. Then it may be fixed in position using an adhesive. Thus, this embodiment can avoid dust or shaved particles of the lens frame 54, as may be generated during a focus adjustment, from adhering to the image sensor surface of the CMOS image pickup device 23, thereby degrading the quality of images detected by the image pickup device.

A substrate 56 that is fitted with white LEDs 25 is mounted to the lens frame 54, and an electronic chip 27 that includes an LED driving circuit for driving the white LEDs 25 is mounted to the rear side of the substrate 56. Moreover, a diffusing plate 25a is mounted to the front surface of each of the white LEDs 25. The other components of this embodiment will not be separately discussed, as they are identical to those previously discussed for FIGS. 2 and 7. Furthermore, in this embodiment, the position of the center of the entrance pupil of the objective optical system 52 is also at the axis of the cylindrical case 16, and is coincident with the center of curvature of both the inner and outer surfaces of the transparent cover 17. Just as before, this prevents unwanted light from entering the objective optical system 52. Once again, the radius of curvature of the outer surface of the transparent cover 17 is shown as Ro.

In this embodiment, just as in the previous embodiment, the illuminating rays that are emergent from the white LEDs 25 via the diffusing plates 25a with an intensity ratio of 0.1 of the peak intensity overlap before reaching the near-point of the depth of field of the objective optical system 52. The rays having an intensity ratio of 0.1 of the peak intensity are illustrated in FIG. 8. This embodiment provides the same advantages and effects as provided by Embodiment 2 but omits a frame (namely, the sealing cover 44 in FIG. 7) for fixing the second lens. Accordingly, this embodiment enables the capsule endoscope to be further miniaturized, and for the number of parts to be reduced. Thus, when one considers the manufacturing tolerance of parts affecting the overall operation of the assembled device, this embodiment enables the optical performance, in general terms, to be increased.

Furthermore, the cover glass 55 need not be mounted so as to closely adhere to the entire image sensor surface of said CMOS image pickup device. Instead, the cover glass 55 can be mounted on the image sensor surface with a small gap by forming small protrusions at peripheral portions of the surface of the cover glass, and the cover glass may contact and be affixed to the image sensor surface at the protrusions.

Figure 9:
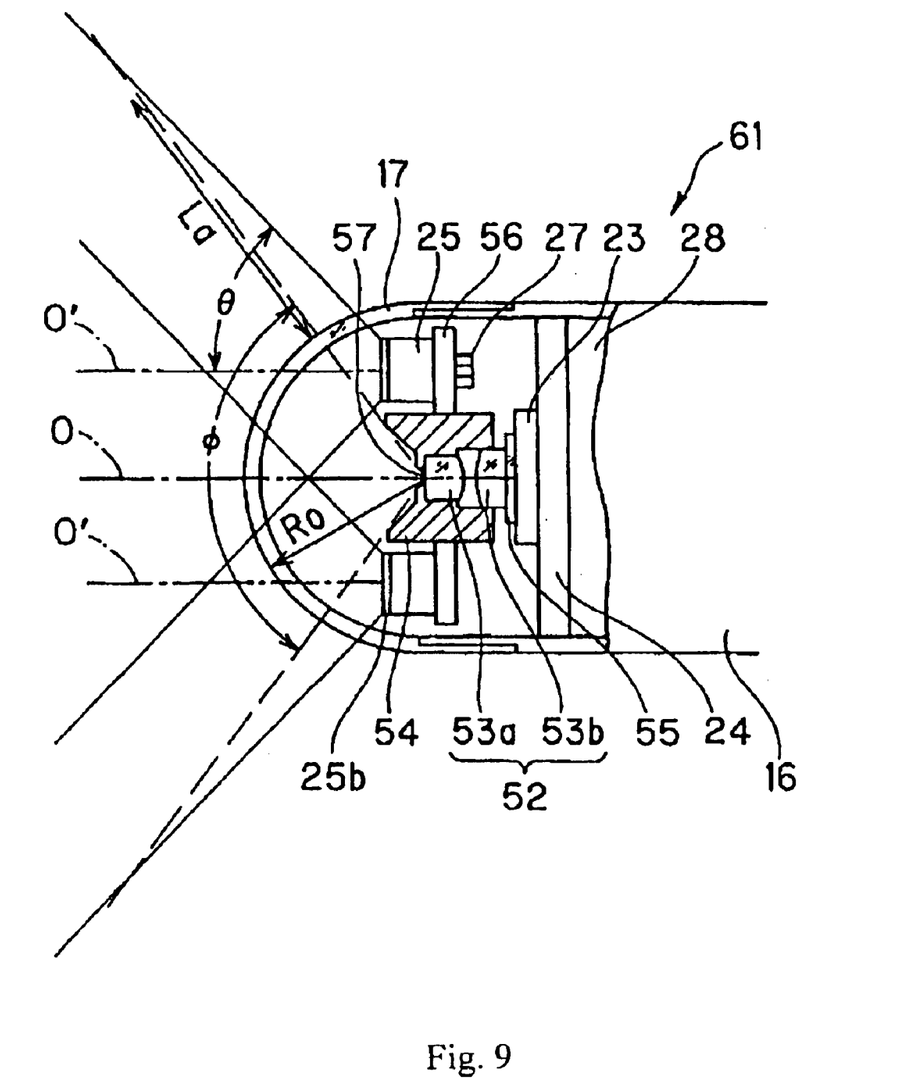
FIG. 9 is a partial cross-sectional diagram showing components of a capsule endoscope according to a modification to Embodiment 3.

FIG. 9 is a partial cross-sectional diagram showing components of a capsule endoscope according to a possible modification to Embodiment 3. The construction of this capsule endoscope 61 is the same as that shown in FIG. 8, except in this embodiment the diffusion plates 25b have a lesser diffusion function than the diffusion plates 25a shown in FIG. 8. Accordingly, the angle of emergence θ becomes narrower than the case of FIG. 8. In this modification, the angle of emergence θ of the LED, which has an intensity ratio of 0.1, is smaller than the half angle of view ($\phi/2$) of the objective lens. And, the illuminating light ray at an angle θ intersects with the outer periphery line of the field angle φ at a point farther than the far point of the depth of field of the objective optical system. In this modification, the rays having a normalized ratio of 0.1 overlap before reaching the near point of the depth of field of the objective optical system 52, just as in the embodiment shown in FIG. 8. This modification also enables more even illumination to be provided within the field of view at the outer peripheral regions than does Embodiment 3.

Figure 10:
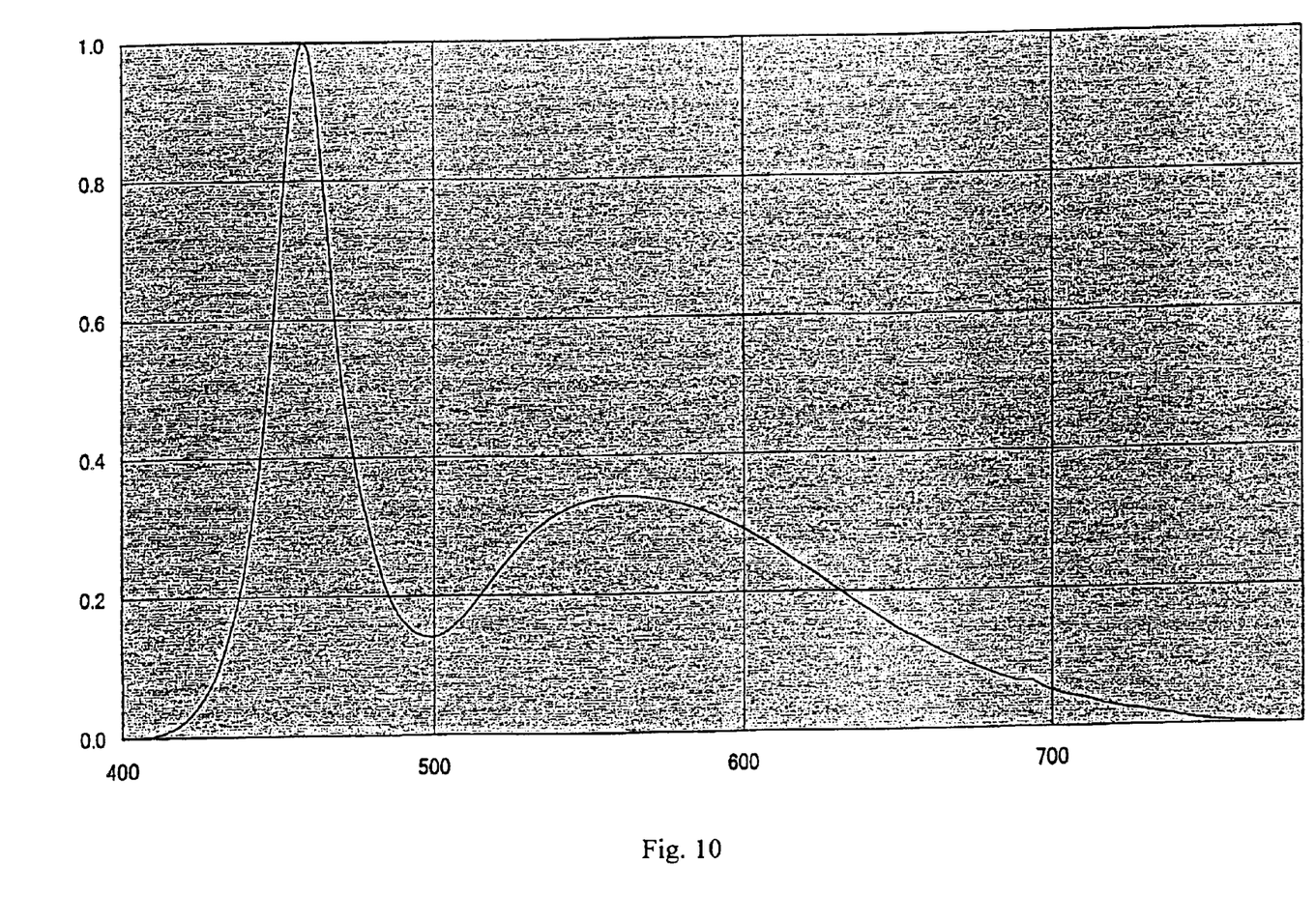
FIG. 10 shows the normalized spectral emission plotted on the Y-axis versus the emitted wavelength (in mm) plotted on the X-axis.

FIG. 10 shows an example of the spectral emission characteristic of the white LEDs 25. The Y-axis indicates the normalized relative intensity (i.e., the maximum intensity has been normalized to unity) that is emitted from a white LED, and the X-axis is the emitted wavelength, in nm. As can be seen in FIG. 10, the light intensity of a white LED has a peak intensity around 450 nm. As a result, when this light is used as an illumination light source for imaging, a natural color balance is not automatically obtained in the reproduced image. Therefore, a color correction filter 26 is used to improve the color balance. The color correction filter 26 should have an optical property which attenuates (i.e., reduces) the intensity of transmitted light near 450 nm.

Figure 11:
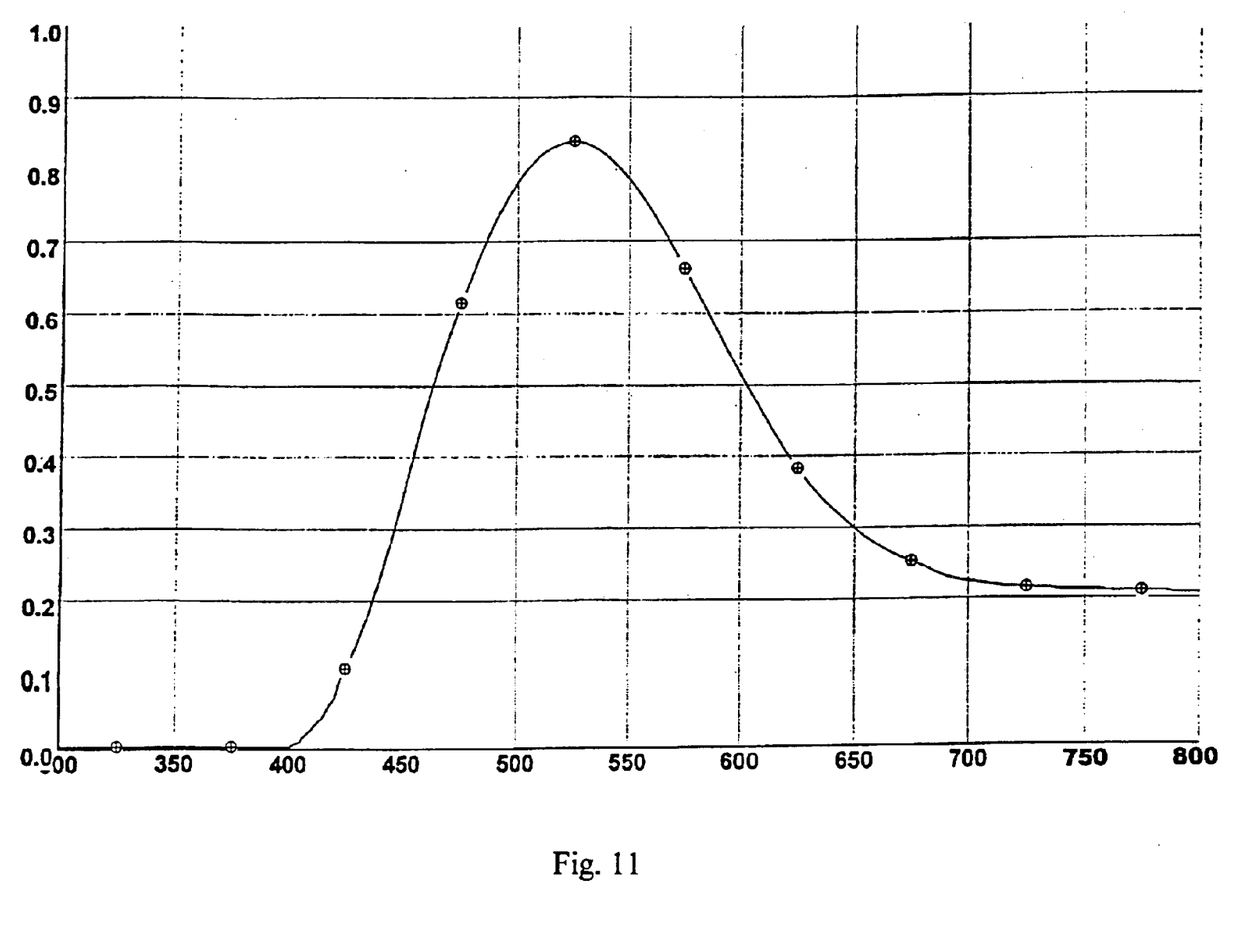
FIG. 11 shows the transmittance plotted on the Y-axis versus the emitted wavelength (in nm) plotted on the X-axis of a color correction filter that is formed of Schott Glass optical material VG 9 having a thickness T equal to 0.5 mm.

FIG. 11 is an example of a glass material VG 9 (available from SCHOTT Glass Mainz) having a spectral transmittance that is suitable for use as the color correction filter 26. This spectral transmittance is obtained when the glass material is formed as a filter having a thickness of 0.5 mm. This glass material absorbs light at wavelengths near 450 nm (the transmittance is around 0.3, as shown in FIG. 11) and serves to reduce the intensity of light near 450 nm. By using this glass material for the color correction filter 26, the color balance of the reproduced image can be improved, and the image looks as if it is photographed using natural light for illumination.

Figure 12:
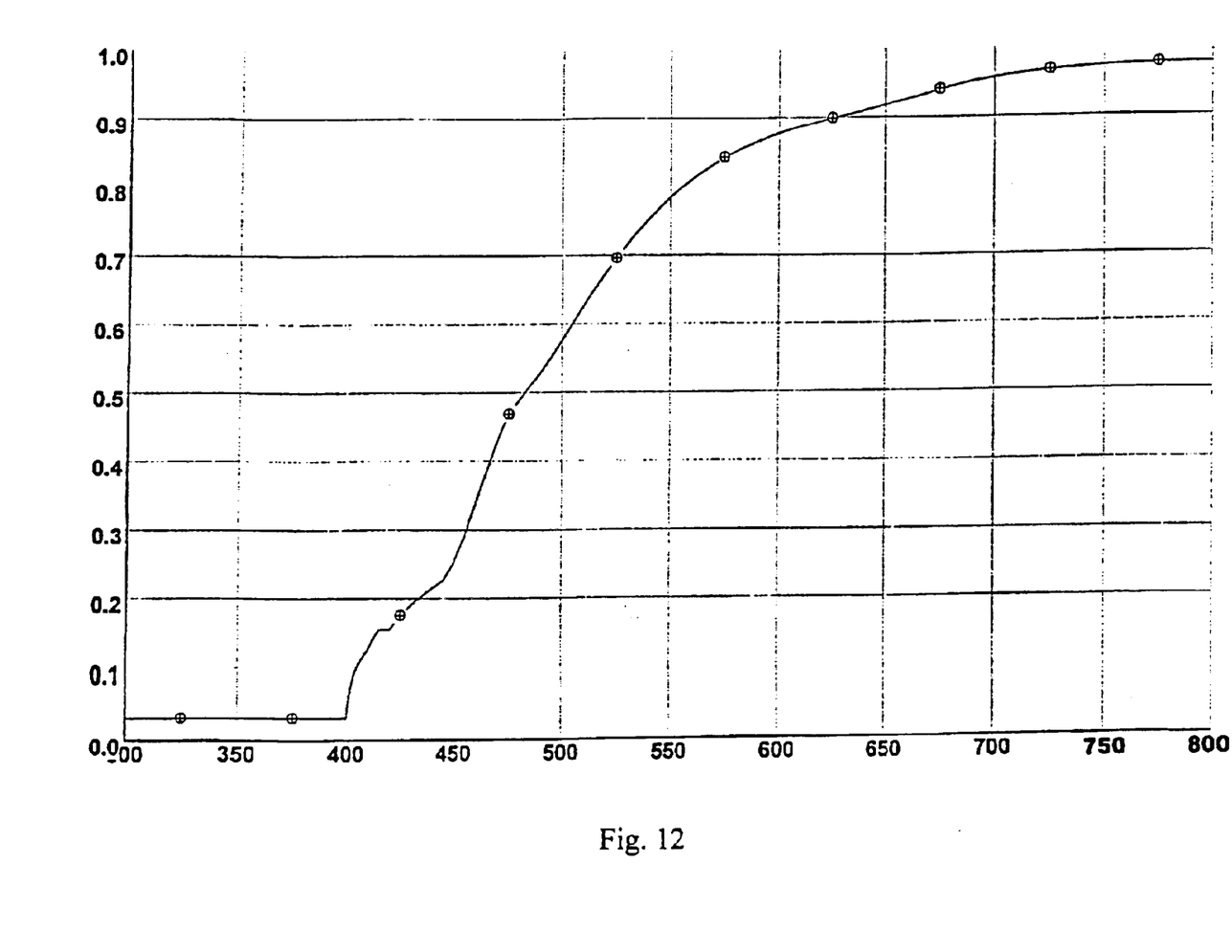
FIG. 12 shows the transmittance plotted on the Y-axis versus the emitted wavelength (in nm) plotted on the X-axis of a color correction filter that is formed of Schott Glass optical material FG 13 having a thickness T equal to 0.6 mm.

FIG. 12 shows another example of a spectral transmittance of a glass suitable for the color correction filter 26. This transmittance is obtained when the glass material FG 13 (available from SCHOTT Glass Mainz) is formed as a filter having a thickness of 0.6 mm. This glass material also absorbs light at 450 nm and serves to reduce the intensity of light near 450 nm. By using this glass material for the color correction filter 26, the color balance of the reproduced image can also be improved so that the image looks as if it is photographed using natural light for illumination.

These color correction filters can be used as the color correction filter 26. A light reflection filter that is composed as a multi-layered interference thin film and has similar spectral transmittance to that of the above-mentioned glass is an example of other types filters that may be used.

The invention being thus described, it will be obvious that the same may be varied in many ways. For example, combinations of the features described in the preferred embodiments may be selectively used. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A capsule endoscope comprising:
   lighting means that includes at least two light sources;
   a light diffuser arranged in front of each of the at least two respective light sources;
   an image pickup means that includes an objective optical system; and
   a transparent cover that may be attached to a capsule body so as to enclosed the lighting means, the light diffusers and the image pickup means; wherein
   said at least two light sources are arranged at the periphery of the objective optical system, and
   rays having a normalized intensity ratio of 0.1 from the at least two light sources intersect prior to reaching the near point of the depth of field of the objective optical system, said intersection point being within the interior region of said capsule body with transparent cover attached.

2. The capsule endoscope as set forth in claim 1, wherein the angle of light distribution of said rays having a normalized intensity ratio of 0.1 is at least 115°.

3. The capsule endoscope as set forth in claim 1, wherein said at least two light sources are white LEDs, and further including at least one color correction filter that is arranged in front of said image pickup means, inside said objective optical system, on the inner surface of said transparent cover or in front of said white LEDs.

4. The capsule endoscope described in claim 1, wherein the outer surface of said lighting means lies to the object side of a plane that passes through the most object side of the objective optical system.

5. A capsule endoscope comprising:
   lighting means that includes at least two light sources;
   an image pickup means that includes an objective optical system; and
   a transparent cover that may be attached to a capsule body so as to enclosed the lighting means and the image pickup means; wherein
   said at least two light sources are arranged at the periphery of the objective optical system, and
   rays having a normalized intensity ratio of 0.5 from the at least two light sources intersect prior to reaching the near point of the depth of field of the objective optical system.

6. The capsule endoscope as set forth in claim 5, wherein the angle of light distribution of said rays is at least 45°.

7. The capsule endoscope as set forth in claim 5, wherein the outer surface of said lighting means lies to the object side of a plane that passes through the most object side of the objective optical system.

8. A capsule endoscope comprising:
   lighting means that includes at least two light sources;
   a light diffuser arranged in front of each of the at least two respective light sources;
   an image pickup means that includes an objective optical system; and
   a transparent cover that may be attached to a capsule body so as to enclose the lighting means, the light diffuser, and the image pickup means; wherein
   said at least two light sources are arranged at the periphery of the objective optical system, and
   rays having a normalized intensity ratio of 0.1 from the at least two light sources intersect prior to reaching the outer surface of the transparent cover.

9. The capsule endoscope as set forth in claim 8, wherein the angle of light distribution of said rays is at least 115°.

10. The capsule endoscope as set forth in claim 8, wherein said at least two light sources are white LEDs, and further including at least one color correction filter that is arranged in front of said image pickup means, inside said objective optical system, on the inner surface of said transparent cover or in front of said white LEDs.

11. The capsule endoscope according to claim 8, wherein:
    the outer surface of said lighting means lies to the object side of a plane that passes through the most object side of the objective optical system.

12. A capsule endoscope comprising:
    lighting means that includes at least two light sources;
    an image pickup means that includes an objective optical system; and
    a transparent cover that may be attached to a capsule body so as to enclosed the lighting means and the image pickup means; wherein
    said at least two light sources are arranged at the periphery of the objective optical system, and
    rays from said at least two light sources having a normalized intensity of 0.5 intersect prior to reaching the outer surface of the transparent cover.

13. The capsule endoscope as set forth in claim 12, wherein the angle of light distribution of said rays is at least 45°.

14. The capsule endoscope as set forth in claim 12, wherein said at least two light sources are white LEDs, and further including at least one color correction filter that is arranged in front of said image pickup means, inside said objective optical system, on the inner surface of said transparent cover or in front of said white LEDs.

15. The capsule endoscope as set forth in claim 12, wherein the outer surface of said lighting means lies to the object side of a plane that passes through the most object side of the objective optical system.

* * * * *